(12) United States Patent
Kuwano et al.

(10) Patent No.: US 9,358,162 B2
(45) Date of Patent: Jun. 7, 2016

(54) WEARING ARTICLE

(75) Inventors: Seiichi Kuwano, Kagawa (JP); Yuki Hashino, Kagawa (JP); Shunsuke Masaki, Kagawa (JP)

(73) Assignee: Unicharm Corporation, Ehime (JP)

( * ) Notice: Subject to any disclaimer, the term of this patent is extended or adjusted under 35 U.S.C. 154(b) by 718 days.

(21) Appl. No.: 13/700,781

(22) PCT Filed: May 30, 2011

(86) PCT No.: PCT/JP2011/062329
§ 371 (c)(1),
(2), (4) Date: Nov. 29, 2012

(87) PCT Pub. No.: WO2011/152336
PCT Pub. Date: Dec. 8, 2011

(65) Prior Publication Data
US 2013/0079742 A1      Mar. 28, 2013

(30) Foreign Application Priority Data

May 31, 2010  (JP) ................................. 2010-125231

(51) Int. Cl.
*A61F 13/15*    (2006.01)
*A61F 13/49*    (2006.01)
*A61F 13/496*   (2006.01)

(52) U.S. Cl.
CPC ......... *A61F 13/49011* (2013.01); *A61F 13/496* (2013.01); *A61F 13/49061* (2013.01); *A61F 13/49009* (2013.01); *A61F 13/49015* (2013.01)

(58) Field of Classification Search
CPC .................... A61F 13/49015; A61F 13/49011; A61F 13/49009
USPC ............ 604/385.24, 385.25, 385.26, 385.27, 604/385.28, 385.29, 385.3
See application file for complete search history.

(56) References Cited

U.S. PATENT DOCUMENTS

2005/0107764 A1    5/2005  Matsuda et al.
2010/0312214 A1   12/2010  Shimada et al.

FOREIGN PATENT DOCUMENTS

| EP | 1384459 | * | 1/2004 | ............. A61F 13/15 |
| EP | 2260811 | * | 12/2009 | ............. A61F 13/15 |

(Continued)

OTHER PUBLICATIONS

International Search Report based on corresponding PCT application No. PCT/2011/062471 dated Sep. 13, 2011 (4 pgs).

(Continued)

*Primary Examiner* — Jacqueline Stephens
(74) *Attorney, Agent, or Firm* — Brinks Gilson & Lione (57) ABSTRACT

A wearing article having a waist-opening that can be easily folded back along a fold line extending in a transverse direction without increasing the stiffness in the vicinity of the waist-opening. A diaper includes front and rear waist members and a crotch member. A liquid-absorbent structure of the crotch member is formed outboard of in a longitudinal direction of a core with front and rear flaps exclusively composed of an absorption surface wrapping sheet, a leakage-barrier sheet and a bottom surface wrapping sheet. The front and rear waist members include first regions overlapping the front and rear flaps, respectively, second regions lying adjacent to the associated first regions and third regions lying adjacent to the associated second regions. The front and rear waist members are provided with the first, second and third waist elastics attached between respective inner and outer sheets in the first, second and third regions, respectively. A tensile stress of the first regions and the third regions is adjusted to be lower than that of the second regions.

20 Claims, 7 Drawing Sheets

(56) References Cited

FOREIGN PATENT DOCUMENTS

| | | |
|---|---|---|
| EP | 2 260 811 A1 | 12/2010 |
| JP | 2003-305083 | 10/2003 |
| JP | 2007-511326 A | 5/2007 |
| JP | 2009-119078 | 6/2009 |
| JP | 2009-240694 | 10/2009 |
| JP | 2009-240694 A | 10/2009 |
| JP | 2009-240695 | 10/2009 |
| JP | 2010-069023 | 4/2010 |
| JP | 2010-75463 A | 4/2010 |
| WO | WO 2009/119195 A1 | 10/2009 |
| WO | WO 2009/122803 A1 | 10/2009 |
| WO | WO 2010/032581 A1 | 3/2010 |

OTHER PUBLICATIONS

European extended Search Report from corresponding European application No. 11789739.7 dated Feb. 24, 2015 (6 pgs).

* cited by examiner

WEARING ARTICLE

RELATED APPLICATION

This application is a 35 U.S.C. §371 national phase filing of International Patent Application No. PCT/JP2011/062329, filed May 30, 2011, through which and to which priority is claimed under 35 U.S.C. §119 to Japanese Patent Application No. 2010-125231, filed May 31, 2010.

TECHNICAL FIELD

The present invention relates to wearing articles and more specifically to wearing articles such as disposable diapers, toilet-training pants and incontinence briefs.

BACKGROUND

Conventionally, disposable diapers each formed with a waist-opening and a pair of leg-openings wherein the periphery of the waist-opening is adapted to be folded toward the non-skin-facing side are known. For example, JP 2003-305083 A (PTL 1) discloses a diaper of which a waist-opening provided with a high frictional member formed of, for example, elastomer or urethane foam so that the waist-opening may be folded back along a lower end of this high frictional member, in other words, the high frictional member may serve as a guide line for folding back the high frictional member.

CITATION LIST

Patent Literature

{PTL 1}: JP 2003-305083 A

SUMMARY

Technical Problem

There is a possibility that the high frictional member attached to the waist-opening might unacceptably increase stiffness of the waist-opening as a whole and deteriorate feeling to wear the diaper. Without the high frictional member, however, the waist-opening will be not formed with any fold guide line and, in consequence, it will be difficult to fold back the waist-opening.

An object of the present invention is to provide a wearing article improved so that a waist-opening can be easily folded back along a fold line extending in a transverse direction without increasing a stiffness in vicinities of the waist-opening.

Solution to Problem

The present invention relates to a wearing article having a longitudinal direction and a transverse direction, and including: a chassis including a skin-facing side; a non-skin-facing side opposite to the skin-facing side; a front waist region, a rear waist region and a crotch region extending between these front and rear waist regions; a liquid-absorbent structure extending across the crotch region into the front and rear waist regions; and waist elastics contractibly attached to the front and rear waist regions under tension in the transverse direction. The chassis includes front and rear waist ends extending in the transverse direction and lateral edges extending in the longitudinal direction. The front and rear waist regions are joined to each other along the lateral edges whereupon a waist-opening is defined by the front and rear waist ends and a pair of leg-openings is defined by the front and rear waist ends respectively adjacent to the crotch region and the crotch lateral edges.

In the wearing article, the present invention further includes the following features. The front and rear waist ends are arranged at a distance from the front and rear ends of the liquid-absorbent structure and this distance dimension is uniform in the front and rear waist regions. A dimension in the longitudinal direction of the liquid-absorbent structure overlapping the front and rear waist regions is in the range of 70 to 98% of a total dimension in the longitudinal direction of the front and rear waist regions. The front and rear waist regions respectively include first regions extending from the front and rear waist ends toward the side of the crotch region and at least partially overlapping the liquid-absorbent structure and second regions adjacent to the associated first regions. The first regions are respectively provided with a plurality of first waist elastics extending in the transverse direction contractibly attached under tension to the respective first regions at a distance from the front and rear ends of the liquid-absorbent structure. A tensile stress of the first regions is lower than that of the second regions.

According to one embodiment of the present invention, the respective second regions are provided with a plurality of second waist elastics extending in the transverse direction and contractibly attached thereto under tension and the first waist elastics have a fineness smaller than that of the second waist elastics and a stretch ratio higher than that of the second waist elastics.

According to another embodiment of the present invention, the liquid-absorbent structure includes a liquid-absorbent core, a wrapping sheet adapted to wrap the core and front and rear flaps lying outboard of the core front and rear ends as viewed in the longitudinal direction and respectively defined by the wrapping sheet, wherein the first waist elastics are attached so as to overlap at least partially with the front and rear flaps.

According to even another embodiment of the present invention, a tensile stress of the respective first regions corresponds to 70 through 90% of a tensile stress of the respective second regions.

According to yet another embodiment of the present invention, the front and rear waist regions additionally include third regions lying adjacent to the side of the respective second regions closest to the crotch region and thus the front and rear waist regions are divided into the first regions, the second regions and the third regions wherein a tensile stress of the respective third regions is adjusted to be lower than that of the second regions.

According to still another embodiment of the present invention, a tensile stress of the respective second regions is 15 through 50% higher than that of the respective third regions.

According to a further embodiment of the present invention, the crotch region includes a pair of gasket cuffs extending in the longitudinal direction and spaced apart from each other in the transverse direction and these gasket cuffs are provided with gasket cuff elastics extending in the longitudinal direction and contractibly attached thereto under tension, wherein the gasket cuff elastics are attached at a distance from the front and rear waist elastics lying closest to the side of the crotch region.

According to an even further embodiment of the present invention, distance dimensions between the front and rear waist elastics lying closest to the ends of the respective gasket cuff elastics are respectively in a range of 1 to 25 mm.

Advantageous Effects of Invention

According to one or more embodiments of the present invention, the front and rear waist regions respectively include the first regions extending from the ends of the front and rear waist regions toward the side of the crotch region so as to overlap at least part of the liquid-absorbent structure and elasticized in the transverse direction and the second regions lying adjacent to the associated first regions and elasticized in the transverse direction, wherein the tensile stress of the first region is sufficiently lower than that of the second regions to facilitate the first regions to be expanded in the transverse direction. Such first regions can be easily folded along the front and rear ends of the liquid-absorbent structure and, in this way, the front and rear waist regions can be folded without increasing a stiffness in the vicinity of the waist-opening.

DESCRIPTION OF EMBODIMENTS

FIGS. 1 through 5 illustrate a first embodiment of the present invention and the present invention will be described hereunder on the basis of a disposable diaper as one example of the wearing article.

Figure 1:
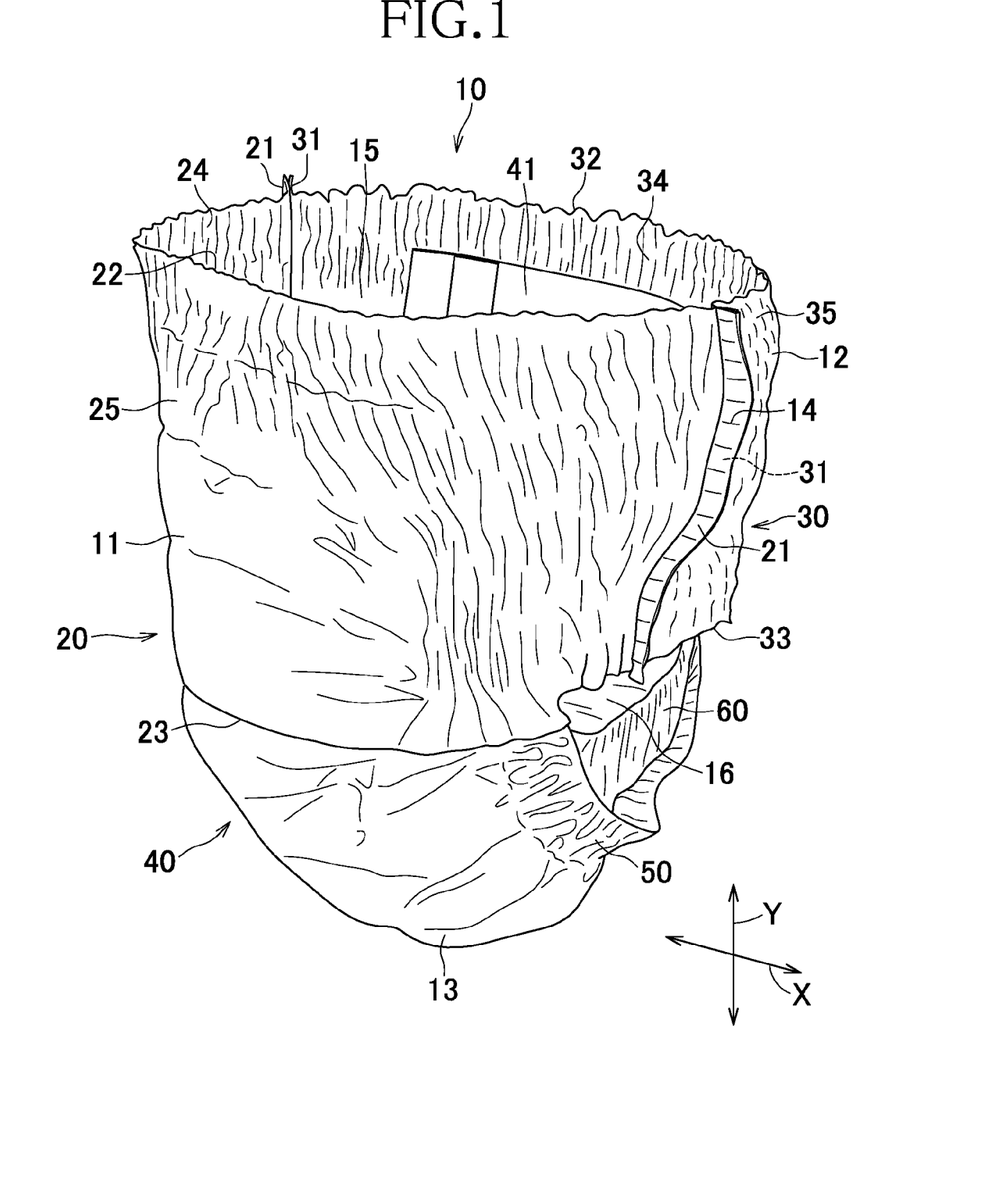
FIG. 1 is a perspective view of a disposable diaper as one example of the wearing article.
Figure 2:
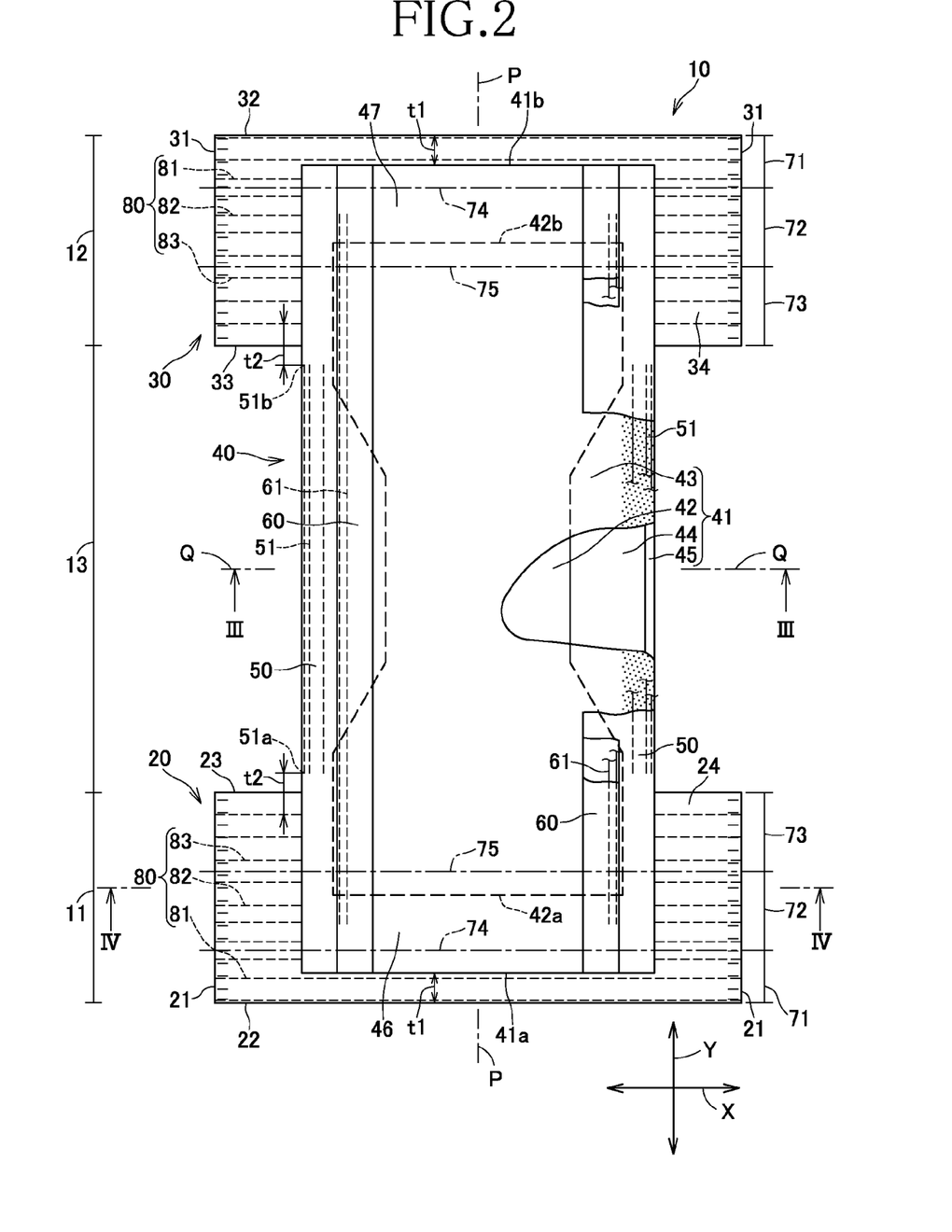
FIG. 2 is a developed plan view of the diaper as viewed from a skin-facing side.
Figure 3:
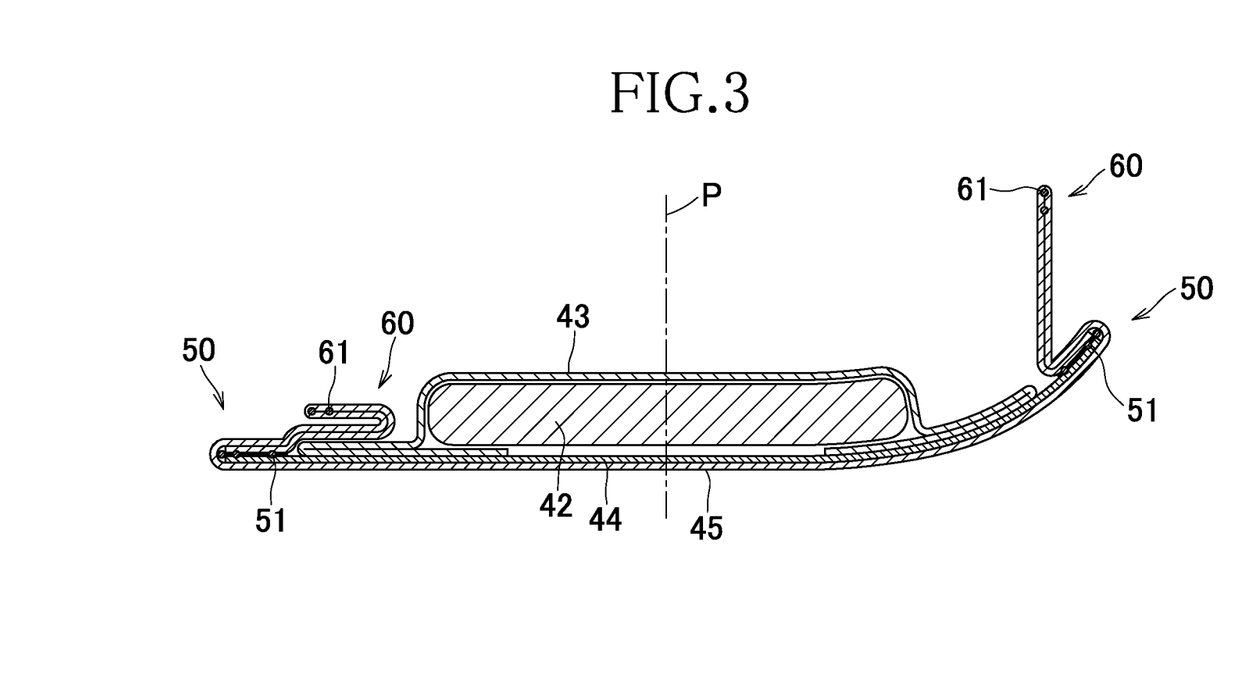
FIG. 3 is a sectional view taken along line in FIG. 2.
Figure 4:
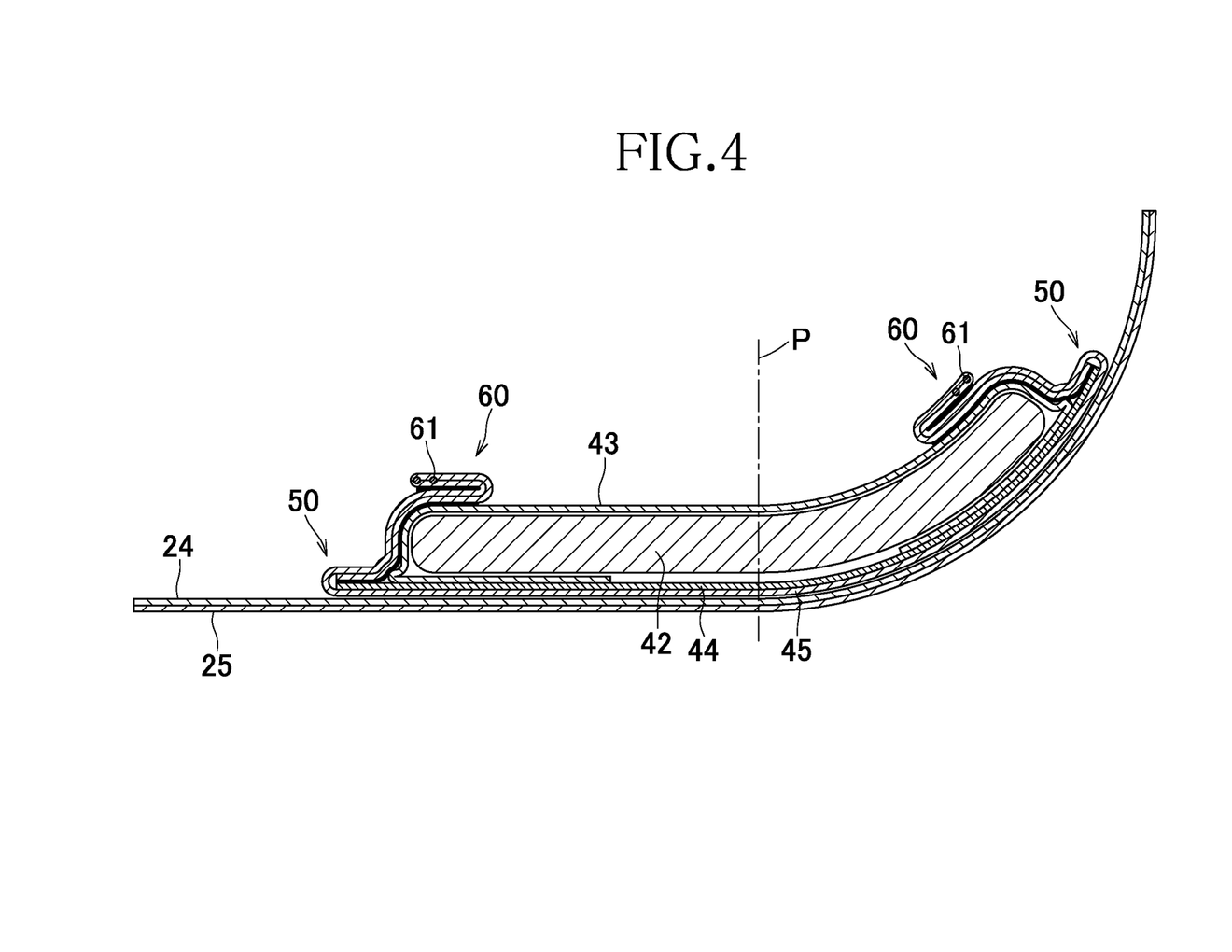
FIG. 4 is a sectional view taken along line IV-IV in FIG. 2.
Figure 5:
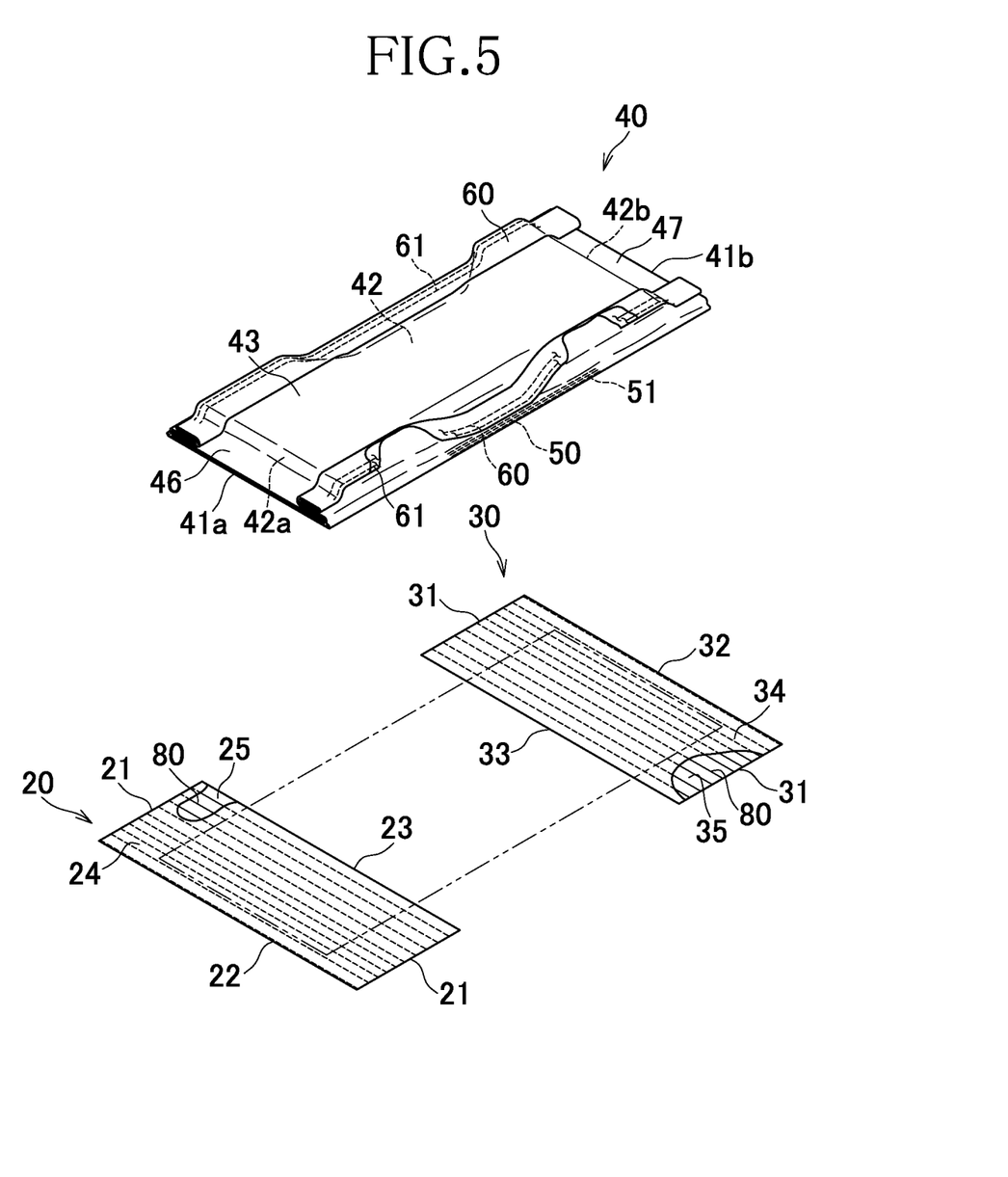
FIG. 5 is an exploded view corresponding to FIG. 2.

FIG. 1 is a perspective view of a disposable diaper 10 with a waist-opening 15 as well as leg-openings 16 being kept in annular states. FIG. 2 is a developed plan view of the diaper 10 as viewed from the skin-facing side with respective elastic members of the diaper being kept in a stretched state to maintain the diaper 10 in flattened state. FIG. 3 is a sectional view taken along line III-III in FIG. 2. FIG. 4 is a sectional view taken along line IV-IV in FIG. 2. FIG. 5 is an exploded view corresponding to FIG. 2. On respective right sides of a longitudinal imaginary center line P-P in FIGS. 3 and 4, the respective elastics are illustrated to be left contract.

The diaper 10 has a longitudinal direction Y and a transverse direction X and includes a skin-facing side, a non-skin-facing side opposite to the skin-facing side, i.e., a garment-facing side, a front waist region 11, a rear waist region 12 and a crotch region 13 extending between the front and rear waist regions 11, 12. The diaper 10 has a longitudinal imaginary center line P-P bisecting a dimension in the transverse direction X and a transversely extending imaginary center line Q-Q bisecting a dimension in the longitudinal direction Y wherein the diaper 10 is shaped so as to be substantially symmetric about the longitudinal imaginary center line P-P as well as about a transversely extending imaginary center line Q-Q.

The diaper 10 includes front and rear waist members 20, 30 spaced apart from each other in the longitudinal direction Y and a crotch member 40 by the intermediary of which the front and rear waist members 20, 30 are connected to each other. The front and rear waist members 20, 30 respectively have lateral edges 21, 31 spaced apart from each other in the transverse direction X. The lateral edges 21, 31 cooperate to form a pair of seams 14 so that the front and rear waist members 20, 30 are joined to each other along these seams 14. Upon being joined in this manner, the waist-opening 15 and a pair of leg-openings 16 are formed. Specifically, the front and rear waist members 20, 30 may be joined to each other along the lateral edges 21, 31 thereof to define the waist-opening 15 by these front and rear waist ends 22, 32 and to define the leg-openings 16 by the front and rear crotch ends 23, 33 adjacent to the crotch member 40 and the lateral edges of the crotch member 40. Regions in which the seams 14 extend in the longitudinal direction Y are designated as the front and rear waist regions 11, 12. The front and rear waist members 20, 30 respectively include the front and rear waist ends 22, 32 adapted to define the waist-opening 15 and the inner ends 23, 33 lying adjacent to the crotch region 13 and adapted to partially define the leg-openings 16. The front and rear waist members 20, 30 respectively include inner sheets 24, 34 lying on the skin-facing side and outer sheets 25, 35 lying on the garment-facing side.

The front and rear waist members 20, 30 and part of the crotch member 40 cooperate together to define the chassis according to the present invention.

The crotch member 40 includes a liquid-absorbent structure 41, gasket cuffs 50 and leakage-barrier cuffs 60. The liquid-absorbent structure 41 includes a liquid-absorbent core 42, an absorbent surface wrapping sheet 43 adapted to wrap an absorbent surface of the core 42 as a wrapping sheet for the core 42, a bottom surface wrapping sheet 45 adapted to wrap a bottom surface of the core 42 and a leakage-barrier sheet 44 interposed between the bottom surface of the core 42 and the bottom surface wrapping sheet 45. As material of the core 42, fluff pulp, superabsorbent polymer particles, or a mixture thereof wrapped with a liquid-pervious sheet such as tissue paper or a fibrous nonwoven fabric may be used. Such core 42 has a constricted shape of which a dimension in the transverse direction X is gradually reduced toward the transversely extending imaginary center line Q-Q.

The core 42 has a dimension in the longitudinal direction Y thereof may be in a range of about 300 to about 410 mm, preferably in a range of about 310 to about 380 mm. The absorbent surface wrapping sheet 43 and the leakage-barrier sheet 44 respectively have a dimension in the longitudinal direction Y thereof larger than the dimension in the longitudinal direction Y of the core 42 and may be in a range of about 350 to about 450 mm, preferably in a range of about 370 to about 430 mm. Such liquid-absorbent structure 41 is formed outboard of the core 42 as viewed in the longitudinal direction Y with front and rear flaps 46, 47 each of which exclusively consists of the absorbent surface wrapping sheet 43, the leakage-barrier sheet 44 and the bottom surface wrapping sheet 45. In each of these front and rear flaps 46, 47, the absorbent surface wrapping sheet 43, the leakage-barrier sheet 44 and the bottom surface wrapping sheet 45 are bonded to each other by bonding means such as hot melt adhesive. According to this embodiment, a dimension in the longitudinal direction Y of the front and rear flaps 46, 47, i.e., a distance from front and rear ends 41a, 41b of the liquid-absorbent structure 41 to front and rear ends 42a, 42b of the core 42 may be about 30 mm. In this regard, the liquid-pervious sheet of the core 42 may extend outward beyond the front and rear ends 42a, 42b if the situation calls for it and, in such case, the front and rear flaps 46, 47 may include liquid-pervious sheets, respectively.

As material of the absorbent surface wrapping sheet 43, a liquid-pervious fibrous nonwoven fabric may be used. More specifically, as this absorbent surface wrapping sheet 43, for example, an air-through fibrous nonwoven fabric, a point bonded fibrous nonwoven fabric or a spunbonded fibrous nonwoven fabric each having a mass per unit area in a range of about 10 to about 25 g/m² may be used.

As material of the leakage-barrier sheet 44, a liquid-impervious plastic film may be used and the bottom surface of the core 42 may be wrapped at least with this sheet 44 to prevent bodily fluids such as urine from leaking out of the diaper 10.

As material of the bottom surface wrapping sheet 45, a moisture-pervious but liquid-impervious fibrous nonwoven fabric may be used. More specifically, as this bottom surface wrapping sheet 45, for example, spunbonded-meltblown-spunbonded (SMS) fibrous nonwoven fabric, a point-bonded fibrous nonwoven fabric or a spunbonded fibrous nonwoven fabric each having a mass per unit area in a range of about 10 to about 25 g/m² may be used.

Outboard of the core 42 as viewed in the transverse direction X, the absorbent surface wrapping sheet 43, the leakage-barrier sheet 44 and the bottom surface wrapping sheet 45 respectively extending outward beyond the core 42 cooperated together to define a pair of the gasket cuffs 50. These sheets are bonded to each other by bonding means such as a hot melt adhesive. In each of the gasket cuffs 50, the bottom surface wrapping sheet 45 forms a sleeve within which gasket cuff elastic 51 extending in the longitudinal direction Y is attached. The gasket cuff elastic 51 includes a plurality of elastic yarns or threads which are contractibly attached under tension. As material of the gasket cuff elastic 51, the elastic yarns or threads each having a fineness of about 620 dtex may be used and may be attached at a stretch ratio of about 280%.

The leakage-barrier cuffs 60 are formed from the bottom surface wrapping sheet 45 extending outward beyond the gasket cuffs 50 and folded back on the liquid-absorbent structure 41 substantially in a Z-shape. Between the layers defined by the both side extensions of the bottom surface wrapping sheet 45, barrier cuff elastics 61 each including a plurality elastic yarns or threads extend in the longitudinal direction Y and are attached under tension. The leakage-barrier cuffs 60 are bonded to the gasket cuffs 50 only along front and rear ends thereof and the remaining regions are not bonded to the gasket cuffs 50. Consequently, the leakage-barrier cuffs 60 are spaced upward from the gasket cuffs 50 under the effect of contractile force of the barrier cuff elastics 61.

During use of the diaper 10, the leakage-barrier cuffs 60 are spaced upward from the absorbent surface wrapping sheet 43 so as to come in close contact with the wearer's inguinal regions and the gasket cuffs 50 also are elasticized in the longitudinal direction Y by the gasket cuff elastics 51 so that the gasket cuffs 50 may be curved toward the wearer's body and kept in close contact with the wearer's thighs. In this way, the leakage-barrier cuffs 60 cooperate with the respective gasket cuffs 50 to define dual cuffs making it possible to prevent bodily fluids such as urine from leaking out beyond the peripheries of the leg-openings.

The bottom surface wrapping sheet 45 is bonded to the respective inner sheets 24, 34 of the front and rear waist members 20, 30 and thereby the front and rear waist members 20, 30 are connected to the crotch member 40. The liquid-absorbent structure 41 is attached to the crotch member 40 so as to overlap the front and rear waist regions 11, 12. A dimension in the longitudinal direction Y of the liquid-absorbent structure 41 overlapping the front and rear waist regions 11, 12 in this manner is in a range of about 70 to about 98%, preferably in a range of about 80 to about 96% and more preferably in a range of about 90 to about 96% of a dimension in the longitudinal direction Y of the front and rear waist regions 11, 12. A distance dimension t1 from the front and rear waist ends 22, 32 of the front and rear waist members to the front and rear ends 41a, 41b of the liquid-absorbent structure 41 may be in a range of about 5 to about 25 mm, preferably in a range of about 10 to about 20 mm. According to this embodiment, the distance dimension t1 is set to about 10 mm.

The gasket cuff elastics 51 are attached to the respective gasket cuffs out of overlapping with respective third waist elastics 83 in the state of the front waist member 20, the crotch member 40 and the rear waist members 30 connected together in this order.

More specifically, the gasket cuff elastics 51 are attached to the respective gasket cuffs so that front and rear ends 51a, 51b of the respective gasket cuff elastics 51 may be spaced apart from the third waist elastics 83 without overlapping with these third waist elastics 83 lying nearest to the crotch region 13. A distance dimension t2 between the respective gasket cuff elastics 51 and the associated third waist elastics 83 may be in a range of about 1 to about 25 mm and, in this embodiment, this distance dimension t2 is set to about 10 mm.

Each of the front and rear waist members 20, 30 includes a first region 71 extending from the front or rear waist end 22 or 32 toward the crotch region 13, a second region 72 being adjacent to the first region 71, and a third region 73 being adjacent to the second region 72. The first region 71 and the second region 72 are divided from each other along an imaginary line 74, and the second region 72 and the third region 73 are divided from each other along an imaginary line 75. In this embodiment, the imaginary lines 74, 75 are respectively located midway in the respective pairs of the adjacent elastics as viewed in the longitudinal direction Y. The first, second and third regions 71, 72, 73 in the front and rear waist regions 11, 12, respectively, are adapted to be connected to each other in annular shape.

The front and rear waist members 20, 30 are respectively provided with waists elastics attached between the inner and outer sheets 24, 25; 34, 35, respectively. More specifically, the first, second and third waist elastics 81, 82, 83 are attached to the first, second and third regions 71, 72, 73, respectively. The first, second and third waist elastics 81, 82, 83 are formed of a plurality of elastic yarns or threads continuously extending from one side of the respective lateral edges 21, 31 to a remaining side of the respective lateral edges 21, 31. The first, second and third waist elastics 81, 82, 83 may be attached under tension in the transverse direction X to the first, second and third regions 71, 72, 73 to elasticize the first, second and third regions 71, 72, 73 in the transverse direction X.

As material of the first waist elastics 81, elastic yarns or threads having a fineness in a range of about 320 to about 620 dtex may be used and arranged at a pitch of in a range of about 4 to 12 mm, preferably in a range of about 5 to 8 mm. In this embodiment, a plurality of elastic yarns or threads having a fineness of 470 dtex are arranged so as to be spaced apart from each other in the longitudinal direction at a pitch of about 8 mm. In this regard, the term "pitch" used herein means a center-to-center distance of the adjacent elastic yarns or threads (this definition is applicable also to the description given hereunder). A stretch ratio of the first waist elastic 81 may be in a range of about 210 to 270% and, in this embodiment, this stretch ratio is set to about 240%. In this regard, the term "stretch ratio" used herein means that, for example, stretch ratio of 200% is the value at the moment the elastic member having a length of about 100 mm was stretched to about 200 mm (this definition is applicable also to the description given hereunder). The elastic yarns or threads constituting the first and rear waist elastics 81 located nearest to the crotch region 13 overlap with the front and rear flaps 46, 47 of the liquid-absorbent structure 41. A dimension in the longitudinal direction Y of the respective first regions 71 may be in a range of about 20 to 40 mm and, in this embodiment, this dimension is set to about 30 mm. The respective second waist elastics 82 are attached to the second regions 72 so as to extend across the front and rear flaps 46, 47 as well as the front and rear ends 42a, 42b and to overlap the core 42 in this manner.

As material of the second waist elastics 82, elastic yarns or threads having a fineness in a range of about 620 to 1240 dtex and arranged at a pitch in a range of about 4 to about 12 mm, preferably in a range of about 5 to about 10 mm. In this embodiment, as material of these second waist elastics 82, a plurality of elastic yarns or threads having a fineness of about 940 dtex is used and arranged so as to be spaced apart from each other in the longitudinal direction Y at a pitch of about 10 mm. A stretch ratio of the second waist elastics 82 may be in a range of about 190 to about 240% and, in this embodiment, this stretch ratio is set to about 200%. A dimension in the longitudinal direction Y of the second regions 72 provided with the second waist elastics 82 may be in a range of about 25 to about 100 mm and, in this embodiment, this dimension is set to about 30 mm.

As material of the third waist elastics 83, elastic yarns or threads having a fineness in a range of about 320 to about 780 dtex may be used and arranged at a pitch in a range of about 4 to about 12 mm, preferably in a range of about 5 to about 10 mm. In this embodiment, a plurality of elastic yarns or threads having a fineness of about 470 dtex are arranged so as to be spaced apart from each other in the longitudinal direction Y at a pitch of about 10 mm. A stretch ratio of the third waist elastics 83 may be in a range of about 190 to about 240% and, in this embodiment, this stretch ratio is set to about 200%.

In the front and rear waist region 11, 12 as have been described above, the stretch ratio of the first regions 71 and the third regions 73 is set to be smaller than the stretch ratio of the second regions 72.

The stretch ratio was measured with use of a method as will be described below.

From the diaper 10 having the lateral edges 21, 31 remaining in a joined state, the first, second and third regions 71, 72, 73 were cut out and used as test pieces, respectively. In the course of cutting out the test pieces, the regions in which the liquid-absorbent structure 41 is present were cut out together with the liquid-absorbent structure 41 so that this structure 41 also may be included in the test pieces. In each of these test pieces, a distance between the inner ends of the opposite seams 14 left in contracted state under the effect of the associated elastics was designated by SW and a distance between the inner ends of the opposite seams 14 stretched in the transverse direction X against contractile force of the respective elastics was designated by PW. A dimension in the longitudinal direction Y of the respective regions was designated by L.

The respective test pieces were fixed to chucks of AUTOGRAPH (manufactured by Shimadzu Corporation) spaced apart from each other by a distance corresponding to SW and then stretched at a chuck velocity of 100 mm/min to a distance of 0.875×PW. The contractile force at the time point that the inter-chuck distance increased up to 0.875×PW was recorded as the total tensile stress Fa (N). Based on the total tensile stress Fa (N)/L×10, a tensile stress F per a width of 10 mm for the respective test pieces was calculated.

According to the measurement result, tensile stress F of the first region 71 was about 0.73 N/10 mm, tensile stress F of the second region 72 was about 0.93 N/10 mm and tensile stress F of the third region 73 was about 0.78 N/10 mm. Tensile stress F of the first region 71 may be in a range of about 0.60 to about 1.05 N/10 mm, tensile stress F of the second region 72 may be in a range of about 0.80 to about 1.45 N/10 mm and tensile stress F of the third region 73 may be in a range of about 0.60 to about 1.20 N/10 mm, wherein tensile stress of the first region 71 may be in a range of about 70 to about 90%, preferably in a range of about 75 to about 85% of tensile stress of the second region 72 and tensile stress of the second region 72 may be about 15 to about 50% larger than that of the third region 73. In this embodiment, tensile stress of the second region 72 is set to be about 15 to about 50% larger than that of the third region 73.

Figure 6:
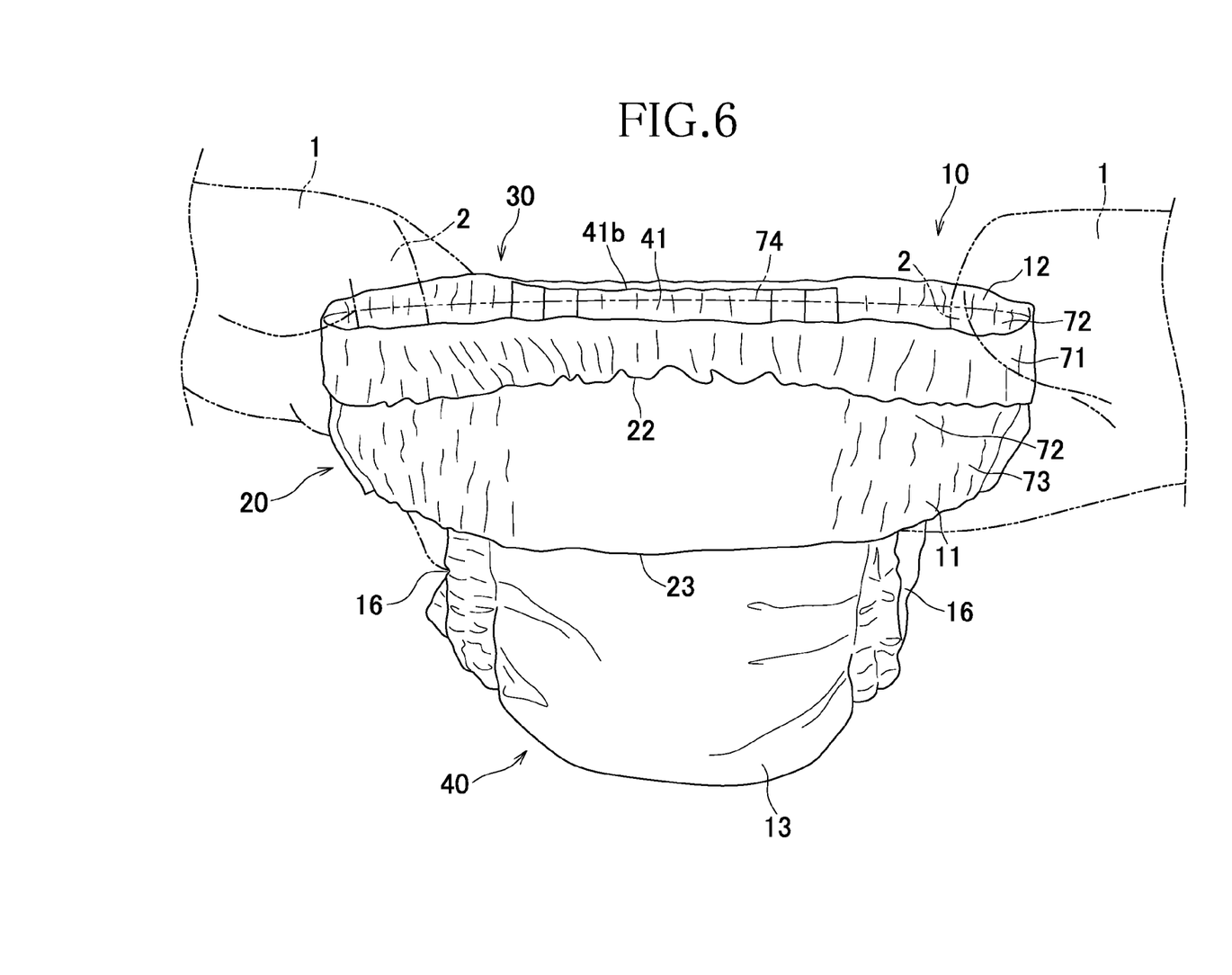
FIG. 6 is a diagram illustrating how to put the diaper on the wearer's body.
Figure 7:
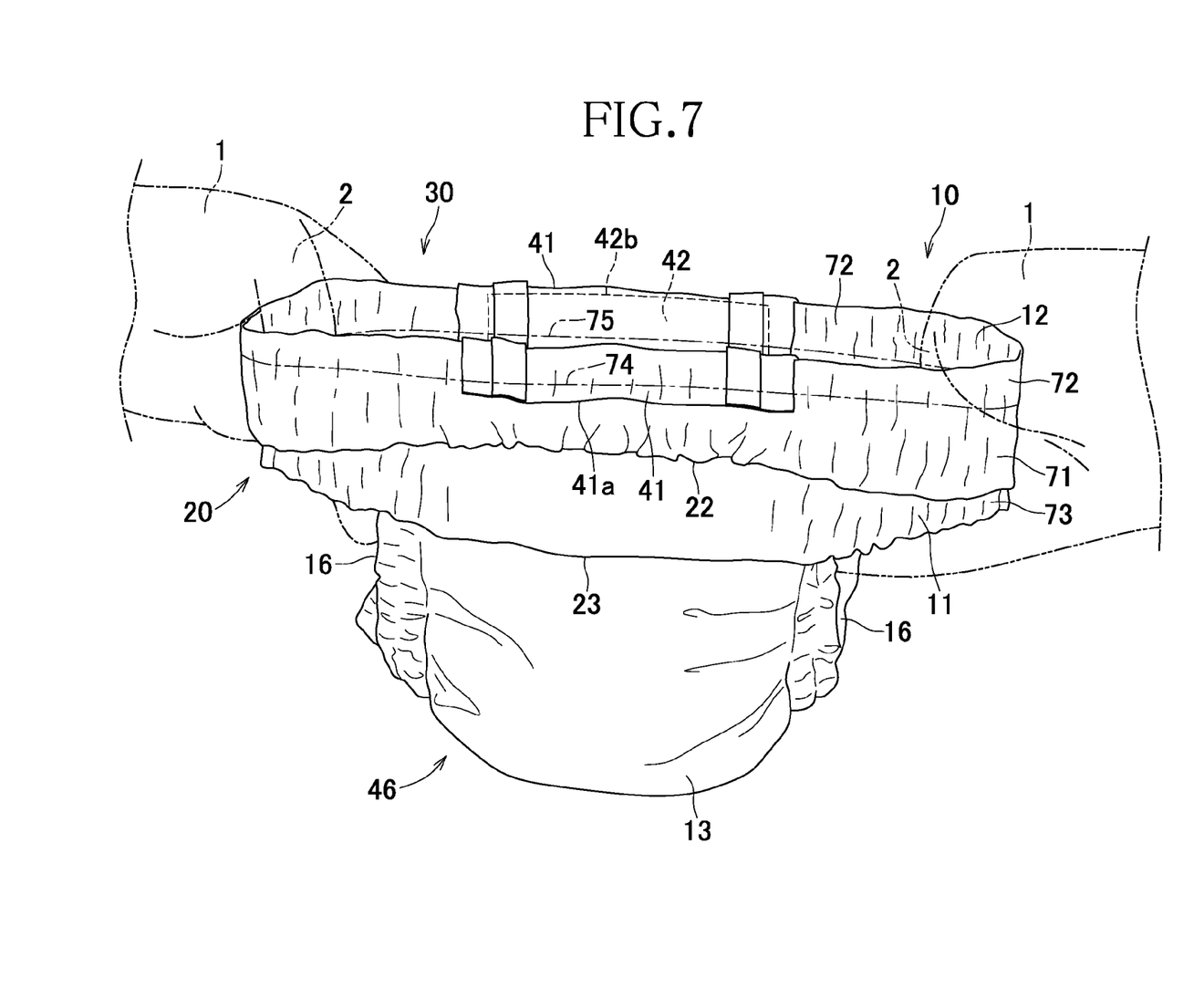
FIG. 7 is a diagram illustrating how to put the diaper on the wearer's body.

FIG. 6 and FIG. 7 illustrate a sequence to put the diaper 10 on a wearer such as an infant as an example. When it is necessary to put the diaper 10 on the wearer, a care person, for example, the mother will pinch the ends 22, 32 of the front and rear waist regions with both hands so that both thumbs 2 may be put on the inside, i.e., the skin-facing side of the diaper 10 and the both thumbs may be moved away from each other in the transverse direction x to expand the diaper 10 in the transverse direction X and to outspread the waist-opening. During this handling to expand the front and rear waist ends 22, 32 of the front and rear waist regions in the transverse direction X, vicinities of the front and rear waist ends 22, 32 of the front and rear waist regions in which the first regions 71 are present are easily expanded since the tensile stress of the first regions are set to be smaller than that of the second regions 72. In addition, in the course of expanding the first regions 71 in the transverse direction X in the manner as has been described, the front and rear waist ends 22, 32 are easily folded along the front and rear ends 41a, 41b of the liquid-absorbent structure 41. Particularly when the first regions 71 are expanded in the transverse direction X with the thumbs 2 inserted into the diaper 10, the ends 22, 32 of the front and rear waist regions are further easily folded outward.

The first regions 71 are provided with the first waist elastics 81 attached thereto which are finer than the second waist elastic members 82 attached to the second regions 72 and, in consequence, the tensile stress of the first regions 71 is sufficiently smaller than that of the second regions 72 to facilitate the first regions 71 to be expanded in the transverse direction X. In addition, the number of sheets layered to form the first regions 71 respectively defined by the front and rear ends 41a, 41b of the liquid-absorbent structure 41 is different from the number of sheets forming the remaining regions and the stiffness of the first regions 71 is correspondingly different from that of the remaining regions. Consequently, the first and second waist regions 11, 12 are easily folded along the front and rear ends 41a, 41b of the liquid-absorbent structure 41. The liquid-absorbent structure 41 lies on the inner side, i.e., on the skin-facing side of the chassis and, therefore, the first regions 71 folded due to the relatively high stiffness thereof are easily folded onto the outside, i.e., the garment-facing side of the chassis.

The waist elastics 80 are attached at spacings between the inner and outer sheets 24, 25; 34, 35, respectively, by bonding means such as hot melt adhesives. In this way, each stiffness of these inner and outer sheets 24, 25; 34, 35 is unlikely to be unacceptably increased. The first regions 71 are composed of these inner and outer sheets 24, 25; 34, 35 and therefore capable of maintaining the flexibility desired for the first regions 71, in other words, sufficient differential in the stiffness in comparison to the other region in which the liquid-absorbent structure 41 is attached. Thus the first regions 71 can be further easily folded along the front and rear ends 41a, 41b of the liquid-absorbent structure 41. Besides, for the reason that the tensile stress of the first waist elastics 81 is set to be higher than that of the second waist elastics 82, an amount of change occurring in the first regions 71 due to the stretchability in the transverse direction X can be made larger than that occurring in the second regions 72 and, as a result, the first regions 71 can be more easily expanded in the transverse direction X and more easily folded.

For the diaper 10 can be put on the wearer's body with the first regions 71 thereof folded onto the non-skin-facing side as has been described above, the diaper 10 can be smoothly put on the wearer's body without the wearer's legs being caught by the ends 22, 32 of the front and rear waist regions. In addition, the diaper 10 can be pulled up with the folded first regions 71 pinched by the care person's fingers and thereby the diaper 10 can be easily put on a desired position.

As illustrated in FIG. 7, the diaper 10 may be further expanded outward in the transverse direction X from the position in FIG. 6 to facilitate the respective second regions 72 of the front and rear waist regions 11, 22 to be folded along the front and rear ends 42a, 42b of the core 42. The second regions 72 delimited by the front and rear ends 42a, 42b of the core 42, respectively, have stiffness sufficiently differentiated from that of the core 42 to be easily folded along the front and rear ends 42a, 42b of the core 42.

In the diaper 10 having the second regions 72 folded along the front and rear ends of the core 42 in this manner, a dimension in the longitudinal direction Y of the front and rear waist regions 11, 12 can be substantially reduced to facilitate the wearer's legs to be guided through the leg-openings 16.

The dimension in the longitudinal direction Y of the front and rear waist regions 11, 12 reduced in this manner facilitates the diaper 10 to be pulled up and facilitates the crotch region 13 of the diaper 10 to be put in close contact with the wearer's crotch.

The dimension in the longitudinal direction Y of the front and rear waist regions 11, 12 can be substantially reduced and consequently the front and rear waist regions 11, 12 can be expanded in the transverse direction X over the entire area thereof. Specifically, not only the first and second regions 71, 72 but also the third regions 73 can be expanded. Particularly for the reason that the tensile stress of the third regions 73 is adjusted to be lower than that of the second region 72, following expansion of the second region, the third region 72 also expanded. The gasket cuff elastics 51 are arranged at a distance from the front and rear crotch ends 23, 33 of the front and rear waist members 20, 30 adjacent to the crotch region, respectively, and, in consequence, the gasket cuff elastics 51 are unlikely to restrict expansion in the transverse direction X of the third regions 73. More specifically, the gasket cuff elastics 51 are contractibly attached in the longitudinal direction Y but the contractile force of these elastics 51 are unlikely to significantly act upon the third regions 73 and restrict expansion in the transverse direction X of the third regions 73.

The diaper 10 is formed symmetrically about the transversely extending imaginary center line Q-Q and therefore the front and rear waist ends 22, 32 may be kept in alignment with each other in the course of forming the diaper 10 with the seams 14 to make the front and rear ends 41a, 41b of the liquid-absorbent structure 41 annularly collinear with the front and rear ends 42a, 42b of the core 42 in the transverse direction X. As a result, it is possible to facilitate the front and rear waist regions 11, 12 to be folded along these annularly collinear ends 41a, 41b, 42a, 42b. In addition, the third waist elastics 83 are attached at a distance from the front and rear ends 41a, 41b of the liquid-absorbent structure 41 without overlapping therewith in any segment of these elastics 83. If the waist elastics are partially collinear with the front and rear ends 41a, 41b of the liquid-absorbent structure 41, the front and rear waist regions 11, 12 might be unnecessarily apt to be folded along the front and rear ends 41a, 41b of the liquid-absorbent structure 41 and, at the worst, the front waist region 11 might be folded outward so as to bite into the wearer's belly during use of the diaper. However, according to the illustrated embodiment, the waist elastics 83 are arranged out of alignment with the front and rear ends 41a, 41b of the liquid-absorbent structure 41 to prevent such undesired folding which might otherwise occur during use of the diaper 1.

The present invention is applicable particularly to the diaper 10 having a relatively small dimension in the longitudinal direction Y, which is most suitable for infants. To ensure that the absorption capacity for bodily fluids such as urine will not be decreased even when the dimension in the longitudinal direction Y of the diaper 10 is relatively small, preferably it should be avoided to reduce a size of the liquid-absorbent structure 41 also correspondingly. Such countermeasure results in that an occupancy of the liquid-absorbent structure 41 in the diaper 10 increases and, particularly in the front and rear waist regions 11, 12, the liquid-absorbent structure 41 occupies in a range of about 70 to about 98% of the dimension in the longitudinal direction Y. The liquid-absorbent structure 41 generally has a relatively high stiffness and the liquid-absorbent structure 41 having a high occupancy would otherwise make it difficult to expand the diaper 10 in the transverse direction X and thus to put the diaper 10 on the wearer's body. However, according to the illustrated embodiment, a tensile stress of the first regions 71 extending close to the waist-opening may be sufficiently reduced to facilitate the diaper 10 to be expanded in the transverse direction X and thereby to facilitate the diaper 10 to be put on an infant's body.

A dimension in the longitudinal direction Y of the diaper 10 according to the present invention may be in a range of about 380 to about 520 mm, preferably in a range of about 400 to about 450 mm and, in the illustrated embodiment, this dimension is set to 400 mm. In a similar fashion, a dimension in the longitudinal direction Y of the crotch member 40 may be in a range of about 350 to about 450 mm, preferably in a range of about 370 to about 430 mm and, in the illustrated embodiment, this dimension is set to about 380 mm. A dimension in the longitudinal direction Y of the front waist member 20 defining the front waist region 11 may be in a range of about 80 to about 130 mm, preferably in a range of about 85 to about 125 mm and, in the illustrated embodiment, this dimension is set to about 90 mm. A dimension in the longitudinal direction Y of the rear waist member 30 defining the rear waist region 12 may be in a range of about 80 to about 190 mm, preferably in a range of about 85 to about 185 mm and, in the illustrated embodiment, this dimension is set to about 90 mm.

While a plurality of elastic yarns or threads are used to elasticize the front and rear waist members 20, 30 in the transverse direction X in the illustrated embodiment, elastics for this purpose are not limited to such elastic yarns or threads but other various types of elastics, for example, belt-like elastics may be used. Similarly, various types of elastics may be used as the gasket cuff elastics 51 and as the barrier cuff elastics 61. While the illustrated embodiment uses the core 42 having a dimension in the transverse direction X being smaller in its midsection than its front and rear sections, it is possible to use a core of which a dimension in the transverse direction X is uniform in all the sections.

The diaper 10 may be formed symmetrically about the transversely extending imaginary center line Q-Q as in the illustrated embodiment to use the diaper 10 without distinguishing the front and rear waist regions 11, 12 from each other. Such embodiment allows, for example, the front waist region 11 to be located on either one of the ventral side or on the dorsal side of the wearer. In other words, it is unnecessary for the care person to make a distinction between front and rear sides of the diaper 10 when the diaper 10 is put on the wearer's body. In this regard, the diaper 10 is not limited to such embodiment formed symmetrically about the transversely extending imaginary center line Q-Q but the diaper 10 may be formed unsymmetrically about the transversely extending imaginary center line Q-Q. For example, the diaper 10 may be implemented so that the rear waist member 30 defining the rear waist region 12 has its inner end adjacent the crotch region 13 further extending into the crotch region 13 so as to cover the wearer's buttocks.

While the first, second and third waist elastics 81, 82, 83 are attached unexceptionally so as to extend continuously between the opposite side edges 21, 31 in the illustrated embodiment, the present invention is not limited to such arrangement. For example, these elastics 81, 82, 83 may be arranged at spacings so that none of these elastics is present or, even if present, contractile force of these elastics may be reduced or lost in a region overlapping the core 42. When the contractile force of these elastics acts in a state spaced apart from one another in the transverse direction X as in such case, the stretch ratio thereof may be calculated on the basis of a formula as follows: stretch ratio={(a dimension in the transverse direction X between the lateral edges 21, 31)/(a length dimension A of the spaced-apart waist elastics in non-stretched state thereof)×100}. The length dimension A in this formula can be calculated on the basis of a formula: {(a dimension in the transverse direction X of a region in which the waist elastics are attached)/(the stretch ratio of the waist elastics)+(a dimension in the transverse direction X of the region in which the contractile force of the waist elastics was reduced or lost)}.

While the front and rear waist regions 11, 12 are respectively divided into the first, second and third regions 71, 72, 73 in the illustrated embodiment, the third regions 73 are not indispensable constituent elements so long as at least the first and second regions having the tensile stress values appropriately differentiated from each other are provided to be adjacent to each other in the front and rear waist regions 11, 12, respectively.

The constituent members of the diaper 10 are not limited to those described in the present specification but the other types of material usually used in the relevant technical field may be used without limitation.

REFERENCE SIGNS LIST 10 diaper (wearing article)
11 front waist region
12 rear waist region
13 crotch region
15 waist-opening
16 leg-openings
20 front waist member (chassis)
21 opposite side edge portions
22 front waist member's outer end
23 front waist member's inner end adjacent to crotch region
30 rear waist member (chassis)
31 lateral edges
32 rear waist end
33 rear crotch end
40 crotch member (chassis)
41 liquid-absorbent structure
41a front end of liquid-absorbent structure
41b rear end of liquid-absorbent structure
42 core
43 absorbent surface wrapping sheet (wrapping sheet)
45 bottom surface wrapping sheet (wrapping sheet)
46 front flap
47 rear flap
50 gasket cuffs
51 gasket cuff elastics
51a front end
51b rear end
71 first region
72 second region
73 third region
80 waist elastics
81 first waist elastics
82 second waist elastics
X transverse direction
Y longitudinal direction

The invention claimed is:

1. A wearing article having a longitudinal direction and a transverse direction, comprising:
a chassis including a skin-facing side, a non-skin-facing side opposite to the skin-facing side, a front waist region, a rear waist region and a crotch region extending between these front and rear waist regions;
a liquid-absorbent member having front and rear ends extending across the crotch region into the front and rear waist regions, the liquid-absorbent member including a liquid-absorbing core, the liquid-absorbing core having front and rear ends; and
waist elastics contractibly attached to the front and rear waist regions under tension in the transverse direction, wherein:
the chassis includes front and rear waist ends extending in the transverse direction and lateral edges extending in the longitudinal direction; and
the front and rear waist regions are joined to each other along the lateral edges whereupon a waist-opening is defined by the front and rear waist ends and a pair of leg-openings is defined by the front and rear waist ends respectively adjacent to the crotch region and the crotch lateral edges, wherein:
the front and rear waist ends are arranged at a distance from the front and rear ends of the liquid-absorbent structure and this distance dimension is uniform in the front and rear waist regions;
a dimension in the longitudinal direction of the liquid-absorbent structure overlapping the front and rear waist regions is in the range of 70 to 98% of a total dimension in the longitudinal direction of the front and rear waist regions;
the front and rear waist regions respectively include first regions extending along the front and rear waist ends which first regions define the waist opening and which first regions at least partially overlap the liquid-absorbent structure and the front and rear waist regions further include second regions located between the first regions and the leg-openings and adjacent to the first regions;
the first regions are respectively provided with a plurality of first waist elastics extending in the transverse direction contractibly attached under tension to the respective first regions at a distance from the front and rear ends of the liquid-absorbent structure;
the front and rear ends of the liquid-absorbent structure are located in the first regions of the front and rear waist regions;

the front and rear ends of the liquid-absorbent core are located in the second regions of the front and rear waist regions; and a tensile stress of the first regions is lower than that of the second regions.

2. The wearing article according to claim 1, wherein the respective second regions are provided with a plurality of second waist elastics extending in the transverse direction and contractibly attached thereto under tension and the first waist elastics have a fineness smaller than that of the second waist elastics and a stretch ratio higher than that of the second waist elastics.

3. The wearing article according to claim 2, wherein the liquid-absorbent structure includes a liquid-absorbent core, a wrapping sheet adapted to wrap the core and front and rear flaps lying outboard of the core front and rear ends as viewed in the longitudinal direction and respectively defined by the wrapping sheet, wherein the first waist elastics are attached so as to overlap at least partially with the front and rear flaps.

4. The wearing article according to claim 3, wherein a tensile stress of the respective first regions corresponds to 70 through 90% of a tensile stress of the respective second regions.

5. The wearing article according to claim 4, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

6. The wearing article according to claim 3, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

7. The wearing article according to claim 2, wherein a tensile stress of the respective first regions corresponds to 70 through 90% of a tensile stress of the respective second regions.

8. The wearing article according to claim 7, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

9. The wearing article according to claim 2, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

10. The wearing article according to claim 2, wherein a tensile stress of the respective second regions is 15 through 50% higher than that of the respective third regions.

11. The wearing article according to claim 1, wherein the liquid-absorbent structure includes a wrapping sheet adapted to wrap the core and front and rear flaps lying outboard of the core front and rear ends as viewed in the longitudinal direction and respectively defined by the wrapping sheet, wherein the first waist elastics are attached so as to overlap at least partially with the front and rear flaps.

12. The wearing article according to claim 11, wherein a tensile stress of the respective first regions corresponds to 70 through 90% of a tensile stress of the respective second regions.

13. The wearing article according to claim 12, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

14. The wearing article according to claim 11, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

15. The wearing article according to claim 1, wherein a tensile stress of the respective first regions corresponds to 70 through 90% of a tensile stress of the respective second regions.

16. The wearing article according to claim 15, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

17. The wearing article according to claim 1, wherein the front and rear waist regions additionally include third regions lying adjacent to the side of the respective second regions closest to the crotch region and thus the front and rear waist regions are divided into the first regions, the second regions and the third regions, wherein a tensile stress of the respective third regions is adjusted to be lower than that of the second regions.

18. The wearing article according to claim 1, wherein a tensile stress of the respective second regions is 15 through 50% higher than that of the respective third regions.

19. The wearing article according to claim 1, wherein the crotch region includes a pair of gasket cuffs extending in the longitudinal direction and spaced apart from each other in the transverse direction and these gasket cuffs are provided with gasket cuff elastics extending in the longitudinal direction and contractibly attached thereto under tension, wherein the gasket cuff elastics are attached at a distance from the front and rear waist elastics lying closest to the side of the crotch region.

20. The wearing article according to claim 19, wherein distance dimensions between the front and rear waist elastics lying closest to the ends of the respective gasket cuff elastics are respectively in a range of 1 to 25 mm.

* * * * *